(12) United States Patent
Perkins et al.

(10) Patent No.: US 9,044,538 B2
(45) Date of Patent: Jun. 2, 2015

(54) AUTOMATIC INJECTOR RAM HOMING

(75) Inventors: Jeffrey A. Perkins, Maineville, OH (US); Mike W. McLean, Liberty Township, OH (US); Victor L. Potter, Middletown, OH (US); Frank M. Fago, Mason, OH (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 111 days.

(21) Appl. No.: 12/811,104

(22) PCT Filed: Aug. 7, 2009

(86) PCT No.: PCT/US2009/053071
§ 371 (c)(1),
(2), (4) Date: Jun. 29, 2010

(87) PCT Pub. No.: WO2010/017430
PCT Pub. Date: Feb. 11, 2010

(65) Prior Publication Data
US 2011/0160580 A1 Jun. 30, 2011

Related U.S. Application Data

(60) Provisional application No. 61/087,452, filed on Aug. 8, 2008.

(51) Int. Cl.
*A61M 5/145* (2006.01)
*A61B 6/00* (2006.01)

(52) U.S. Cl.
CPC ..... *A61M 5/14546* (2013.01); *A61M 2205/106* (2013.01); *A61M 5/14566* (2013.01); *A61M 2205/52* (2013.01); *A61B 6/548* (2013.01)

(58) Field of Classification Search
CPC ............... A61M 5/14546; A61M 5/14566; A61M 2005/14573; A61M 2205/106; A61M 2205/52
USPC .......... 128/DIG. 1; 600/432; 604/65, 67, 131, 604/151, 152, 153, 154, 155, 181
See application file for complete search history.

(56) References Cited

U.S. PATENT DOCUMENTS

| 5,800,397 | A | 9/1998 | Wilson et al. |
| 6,221,045 | B1 | 4/2001 | Duchon et al. |
| 6,652,489 | B2 | 11/2003 | Trocki et al. |

(Continued)

FOREIGN PATENT DOCUMENTS

| EP | 1512423 | 3/2005 |
| EP | 1 911 478 | 10/2007 |

(Continued)

*Primary Examiner* — Kevin C Sirmons
*Assistant Examiner* — Shefali Patel
(74) *Attorney, Agent, or Firm* — Marsh Fischmann & Breyfogle LLP (57) ABSTRACT

A power injector (40) includes a movable ram (74) operable to interface with and move a plunger (90*a/b*) of a syringe (86*a/b*). The power injector (40) may be operable to automatically determine a proper home position for a particular type of the syringe (86*a/b*) to be used in a fluid injection sequence. The power injector (40) may also include a ram homing logic (182) operable to automatically move the ram (74) to the home position after the injection sequence. Such automatic homing of the ram (74) may, for example, be initiated by an end of the injection sequence in preparation for another injection sequence, by opening of a faceplate (102*a/b*), by a user input, or by any combination thereof.

12 Claims, 7 Drawing Sheets

(56) References Cited

U.S. PATENT DOCUMENTS

| | | |
|---|---|---|
| 6,929,619 B2 * | 8/2005 | Fago et al. ................. 604/67 |
| 2004/0158205 A1 * | 8/2004 | Savage ..................... 604/151 |
| 2006/0079765 A1 * | 4/2006 | Neer et al. ................ 600/432 |
| 2007/0100282 A1 | 5/2007 | Small et al. |
| 2007/0260213 A1 | 11/2007 | Williams et al. |
| 2008/0125713 A1 | 5/2008 | Nemoto et al. |
| 2009/0018494 A1 | 1/2009 | Nemoto et al. |
| 2009/0156931 A1 | 6/2009 | Nemoto et al. |

FOREIGN PATENT DOCUMENTS

| | | |
|---|---|---|
| WO | 9965548 | 12/1999 |
| WO | WO 2008/140546 | 11/2008 |

* cited by examiner

AUTOMATIC INJECTOR RAM HOMING

CROSS-REFERENCE TO RELATED APPLICATIONS

This patent application is a U.S. National Stage of PCT/US2009/053071, filed 7 Aug. 2009, which claims priority to and is a non-provisional application of U.S. Provisional Patent Application Ser. No. 61/087,452 entitled "AUTOMATIC INJECTOR RAM HOMING" filed on 8 Aug. 2008. Priority is claimed to each patent application set forth in this Cross-Reference to Related Applications section.

FIELD OF THE INVENTION

The present invention generally relates to injection systems and, more particularly to injection systems and methods related to the automatic movement of an injector ram of an injection system to a home position.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe driver that is incorporated into the powerhead, such that operation of the syringe driver axially advances the associated syringe plunger inside and relative to a barrel of the syringe. One typical syringe driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

The syringes used by the power injector may be pre-filled and/or the power injector may be used to fill the syringes from one or more fluid containers (e.g., containers containing a single dose of medical fluid or bulk fluid containers containing multiple doses of a medical fluid). Pre-filled syringes may include plungers positioned distally relative to a nozzle of the syringe such that fluid may be contained within the syringe. Where fluid containers are utilized, the syringes may be interconnected to the powerhead in an empty condition and then filled by retracting the plunger of the syringe while the fluid container is fluidly connected to the syringe. Accordingly, syringes used in such systems may be supplied with plungers fully advanced (e.g., proximate to the nozzle of the syringe), fully retracted, or in any other appropriate position.

SUMMARY

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid).

Any such power injector may be used for any appropriate application where the delivery of one or more medical fluids is desired, including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

Syringes to be used in the power injectors described herein may be supplied with plungers and may be disposed in various positions relative to the syringe barrel. For example, the syringes may be supplied pre-filled with a medical fluid. In such a case, the plunger may be disposed in a relatively retracted position (e.g., with the plunger distal to a nozzle of the syringe) to accommodate fluid within the syringe barrel. In another example, the syringes may be supplied in an empty state to be filled prior to use. In such a case, the plunger may be disposed in any appropriate position. For example, an empty syringe may be supplied with the piston in a relatively advanced or extended position (e.g., with the plunger proximate to a nozzle of the syringe). In another example, an empty syringe may be supplied with the piston in a relatively retracted position. Aspects described herein may be operable to determine a home position and/or move the ram to the home position for the type of syringe to be used in a patient injection sequence.

A first aspect of the present invention is embodied in a power injector that comprises a ram, syringe type identification logic, a memory unit, and ram homing logic. The memory unit may comprise a lookup table correlating each of a plurality of syringe types to one of a plurality of home positions. As such, for any given syringe type, the lookup table may be used to ascertain a corresponding home position. The ram homing logic may be operable to drive the ram to a home position corresponding to a syringe type upon occurrence of a predetermined condition.

A second aspect of the present invention is embodied in a power injector that comprises a ram, a syringe latch, a syringe latch sensor, and ram homing logic. The ram homing logic may be operable to automatically drive the ram to a home position upon sensing of an opening of the syringe latch by the syringe latch sensor.

Various refinements exist of the features noted in relation to the above-noted first and second aspects of the present invention. Further features may also be incorporated in the first and second aspects of the present invention as well. These refinements and additional features may exist individually or in any combination in relation to each of the first and second aspects. Each of the following features that will be discussed is not required to be used with any other feature or combination of features unless otherwise specified.

In the case of the first aspect, the predetermined condition may comprise any one or more of the following: the removal of a syringe, the unlatching of a syringe from the power injector; the completion of an injection sequence; and fluidly disconnecting a patient from the power injector. The first aspect may further include a syringe latch. A sensor may be arranged to indicate if the syringe latch is latched.

In an embodiment, the power injector may further comprise a syringe sensor. The syringe sensor may be an optical sensor, a radio frequency identification (RFID) tag reader, or any other appropriate sensor or combination of sensors. In an arrangement, the power injector may further include a ram position encoder.

In an embodiment, the power injector may further comprise a faceplate. The faceplate may include a syringe mounting member. The faceplate may be configured for a first type of syringe and the faceplate type may be communicated to the power injector. For example, the faceplate type may be communicated through a sensor of the power injector sensing an attribute of the faceplate that corresponds to the faceplate type.

In an arrangement, the power injector may comprise a faceplate mounting member and a faceplate. The faceplate may include a syringe mounting member. Such a power injector may be operable to determine a faceplate type of the faceplate when the faceplate is interconnected to the faceplate mounting member. The power injector may further comprise a faceplate sensor. The faceplate sensor may be operable to sense the presence of a faceplate installed on the power injector. The faceplate sensor may be operable to sense a faceplate type of a faceplate installed on the power injector. The faceplate sensor may be operable to distinguish a faceplate type based on sensing at least one magnet of the faceplate.

A third aspect of the present invention is embodied in a method of moving an injector ram of a power injector to a home position. The method comprises the power injector identifying a syringe type mounted to the power injector, obtaining a home position for the syringe type identified in the identifying step, detecting an event, and automatically moving the injector ram to the obtained home position in response to the detecting of the event.

Various refinements exist of the features noted in relation to the above-noted third aspect of the present invention. Further features may also be incorporated in the third aspect of the present invention as well. These refinements and additional features may exist individually or in any combination in relation to each of the first and second aspects. Each of the following features that will be discussed is not required to be used with any other feature or combination of features unless otherwise specified.

In an embodiment, the detected event may include one or more of the following: unlatching a faceplate of the power injector; completing an injection sequence with the power injector; receiving a user input, and sensing, by the power injector, a removal of a syringe form the power injector.

In an arrangement, the obtaining step may comprise the power injector looking up, in a lookup table, the home position corresponding to the identified syringe type. In an embodiment, the method may further comprise opening a faceplate.

In an embodiment, the identifying step may include determining a faceplate type of a faceplate interconnected to a faceplate mounting member of the power injector. The faceplate type may correspond to the syringe type. The determining may comprise sensing at least one attribute of the faceplate. The determining may comprise sensing at least one magnet of the faceplate.

In an embodiment, the method may further comprise removing a used syringe from the power injector after the moving step and then installing a new syringe into the power injector.

A fourth aspect of the present invention is embodied in a method of moving an injector ram of a power injector to a home position. The method comprises detecting an unlatching of a syringe latched to the power injector and automatically moving the corresponding injector ram to a home position.

Various refinements exist of the features noted in relation to the above-noted fourth aspect of the present invention. Further features may also be incorporated in the fourth aspect of the present invention as well. These refinements and additional features may exist individually or in any combination in relation to each of the first through third aspects. Each of the following features that will be discussed is not required to be used with any other feature or combination of features unless otherwise specified.

In an embodiment of the third and/or fourth aspect, the method may further comprise presenting a home button to a user and detecting a pressing of the home button to initiate the moving step. The method may further comprise injecting fluid from the syringe into a patient. The method may further comprise verifying that the patient is disconnected from the power injector prior to the automatically moving step.

Various refinements exist of the features noted in relation to each of the above-noted aspects of the present invention. Further features may also be incorporated in each of the above-noted aspects of the present invention as well. These refinements and additional features may exist individually or in any combination in relation to each of the aspects. That is, each of the features discussed are not required to be used with any other feature or combination of features unless otherwise specified.

DETAILED DESCRIPTION

Figure 1:
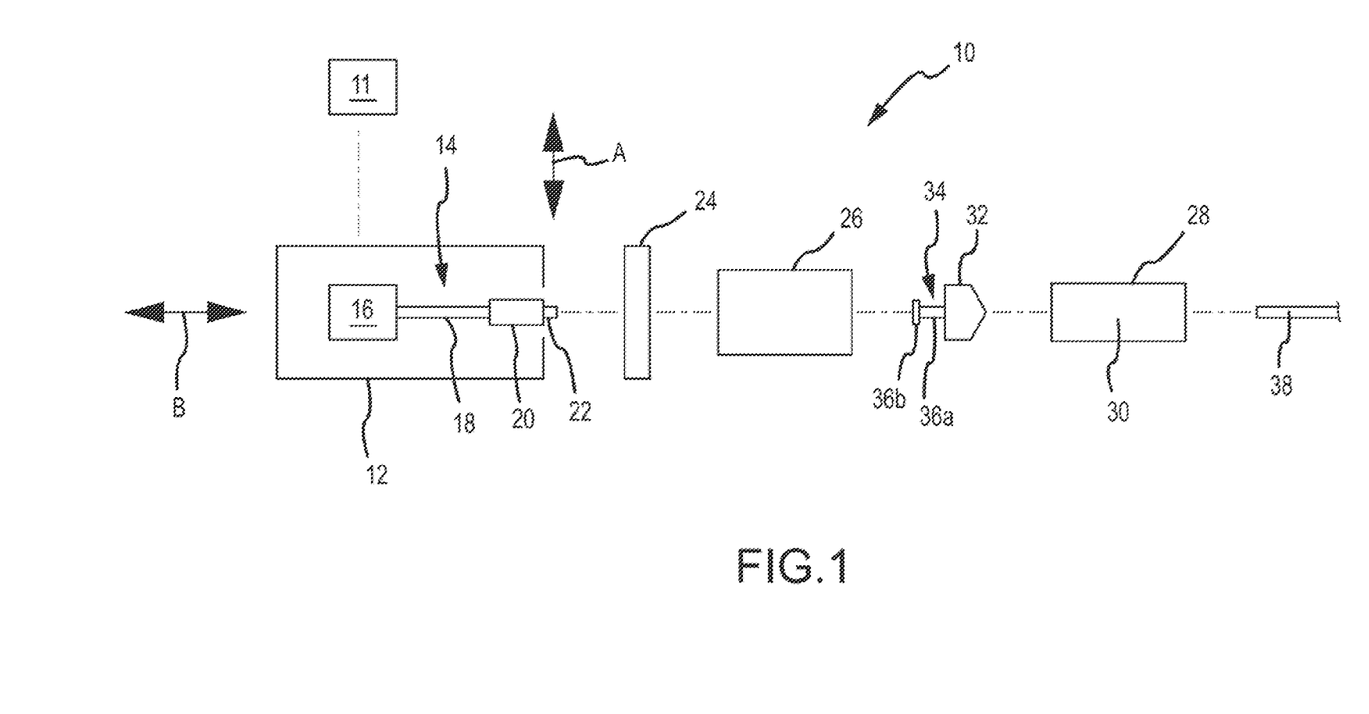
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes the plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g., in different directions along a common axial path).

Retraction of the syringe plunger 32 may be utilized to accommodate a loading of a syringe 28 that is pre-filled with fluid, may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
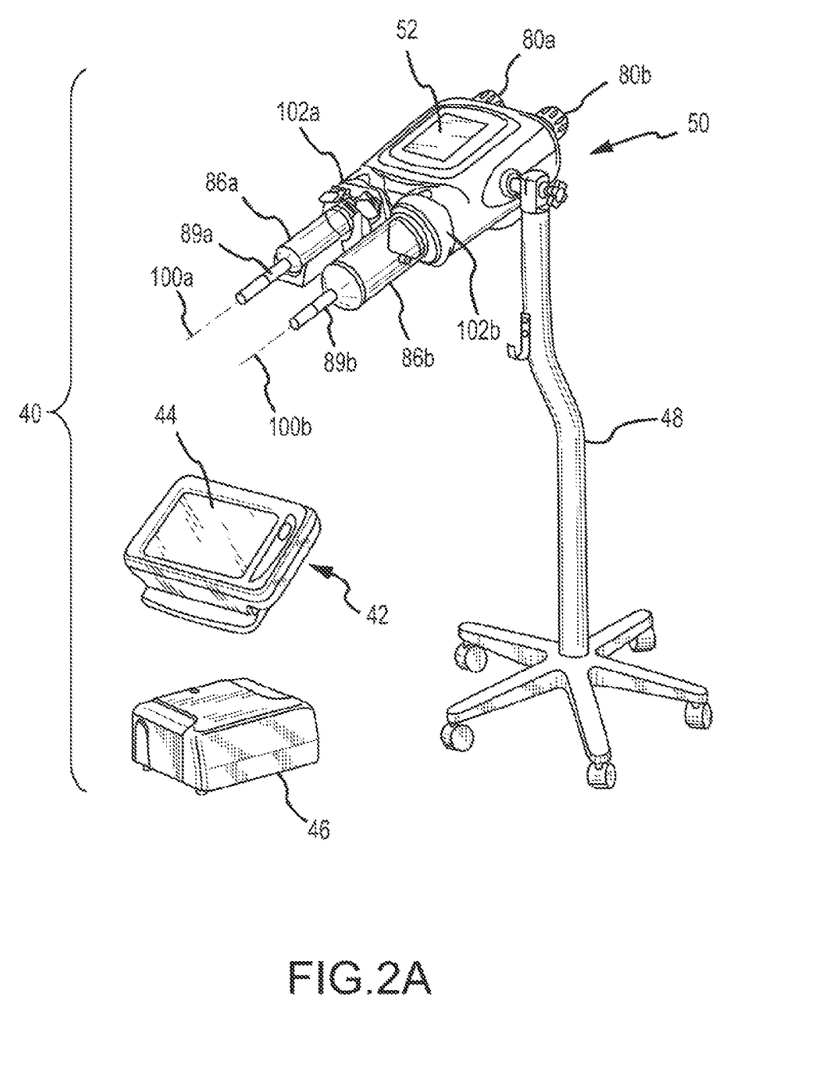
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be drawn into and/or discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading or drawing fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
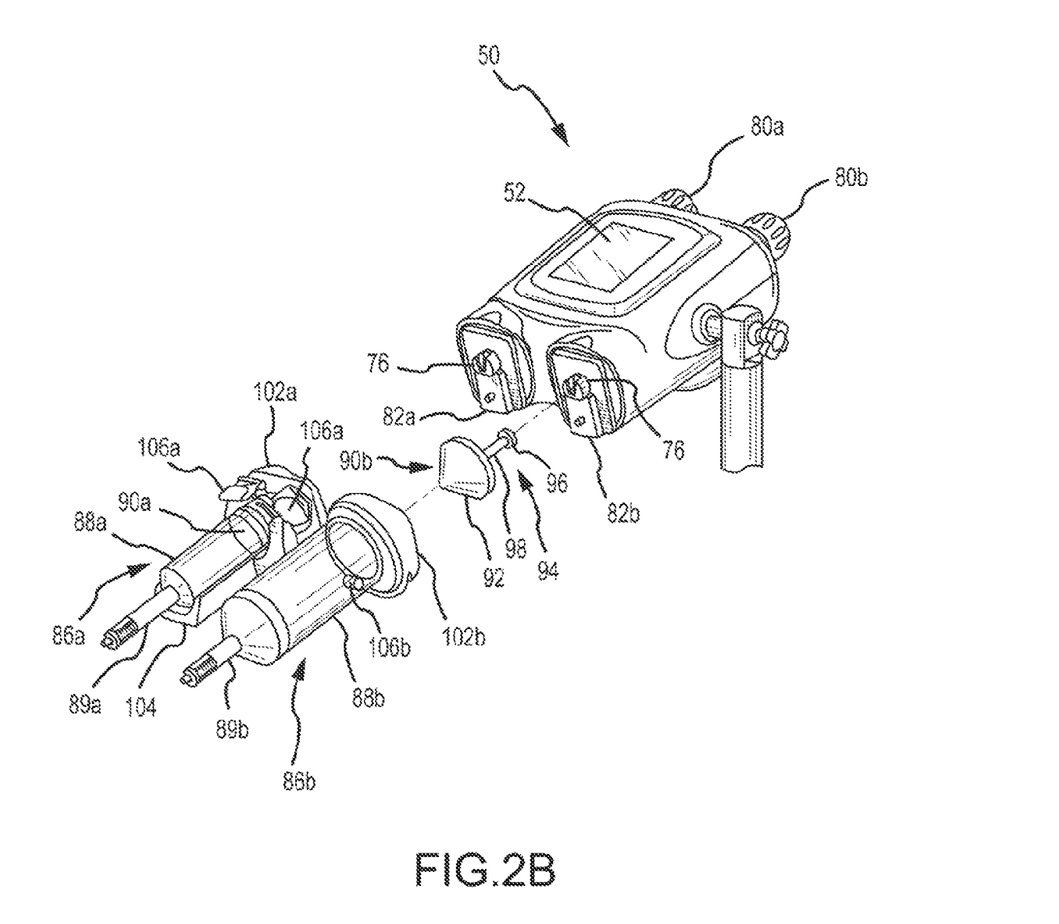
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within the syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b in a first direction along an axis 100b (FIG. 2A) via operation of the powerhead 50 will discharge fluid from within the syringe barrel 88b through a nozzle 89b of the syringe 86b. Movement of the plunger 90b in a direction opposite from the first direction along axis 100b (FIG. 2A) via operation of the powerhead 50 may, where the powerhead 50 is fluidly interconnected to a source of fluid, draw fluid into the syringe barrel 88b through the nozzle 89b of the syringe 86b. An appropriate conduit (not shown) will typically be fluidly interconnected with the nozzle 89b in any appropriate manner to direct fluid to a desired location (e.g., a patient) and/or draw fluid from a desired location (e.g., a fluid container).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
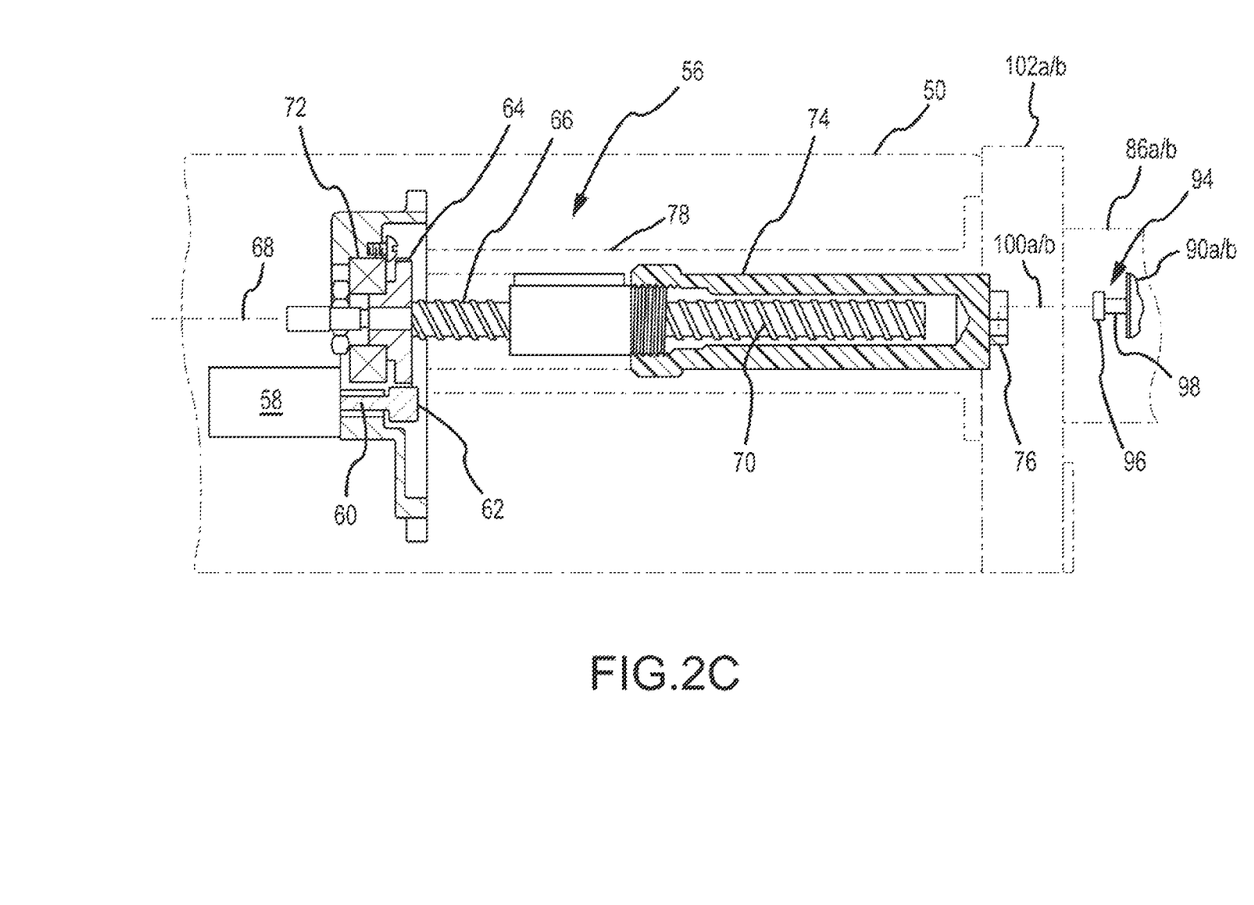
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation CT imaging, MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
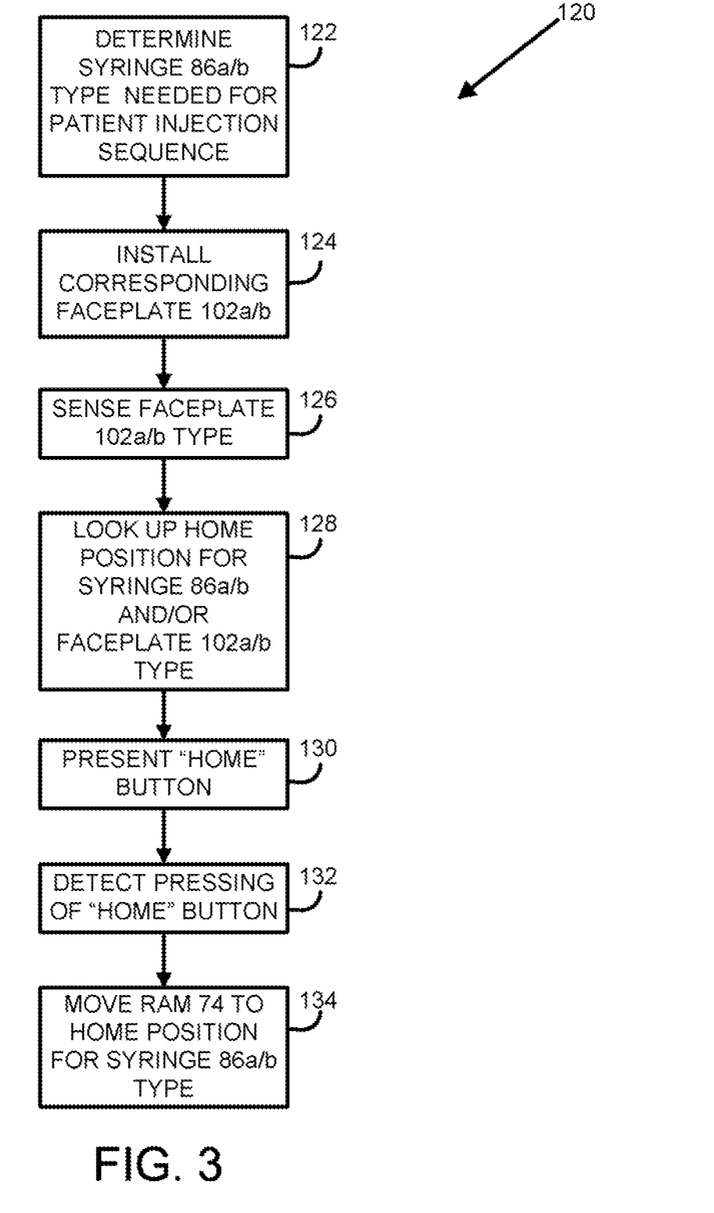
FIG. 3 is a flowchart of a method of moving a ram of a power injector into a home position.

FIG. 3 is a flowchart of a method 120 of moving the ram 74 of power injector 40 to a home position. The individual steps of the method 120 may be performed in any appropriate order. As used herein, "home position" refers to a designated position of the ram 74 where an appropriately configured syringe 86*a/b* (e.g. pre-filled, empty) may be installed onto the faceplate 102*a/b*. The home position may be determined, for example, such that installing and/or removing syringes 86*a/b* is accommodated.

The first step 122 in the method 120 may be to determine the syringe 86*a/b* type needed for the patient injection sequence to be performed. The syringe 86*a/b* type may be dependent on the injection protocol to be enacted. For example, the injection protocol may require injection of a particular fluid type (e.g., contrast, saline) from a pre-filled syringe 86*a/b* of a particular size (e.g. 100 ml, 200 ml). The home position of the ram 74 corresponding to such a pre-filled syringe 86*a/b* may be where the ram 74 is retracted to correspond to and accommodate the retracted (e.g., disposed distal to the nozzle 89*a/b* of the syringe 86*a/b*) plunger 90*a/b* of the pre-filled syringe 86*a/b*. The plunger 90*a/b* of the pre-filled syringe 86*a/b* may be retracted a distance corresponding to the level of fluid in the syringe 86*a/b*.

In another example, the injection protocol may require that the syringe 86*a/b* be empty when installed into the power injector 40. Empty syringes 86*a/b* may be supplied with the plunger 90*a/b* in any appropriate position, including (but not limited to) fully retracted and fully extended (e.g., disposed proximate to the nozzle 89*a/b* of the syringe 86*a/b*). For an empty syringe 86*a/b*, the injection protocol may include the power injector 40 drawing fluid into the syringe 86*a/b* from a fluid source prior to injection of fluid into the patient. Moreover, in such a case, the home position of the ram 74 may correspond to the position of the plunger 90*a/b* in the empty syringe 86*a/b* as supplied. Where the empty syringe 86*a/b* is supplied with the plunger 90*a/b* in an extended position, the home position of the ram 74 may be a corresponding extended position. Where the empty syringe 86*a/b* is supplied with the plunger 90*a/b* in a retracted position, the home position of the ram 74 may be a corresponding retracted position. Where the empty syringe 86*a/b* is supplied with the plunger 90*a/b* in an intermediate position, the home position of the ram 74 may be a corresponding intermediate position.

After determining the syringe 86*a/b* type needed for the patient injection sequence, the next step 124 may be to install the faceplate 102*a/b* that corresponds to the syringe 86*a/b* type to be used. The following step 126 may be for the power injector 40 to sense the type of faceplate 102*a/b* installed on to the power injector 40. A faceplate type sensor 190 is discussed below with reference to FIG. 5. Once the type of faceplate 102*a/b* has been sensed by the power injector 40, the next step 128 may be for the power injector 40 (e.g., home position determination logic 184 (FIG. 5)) to look up a home position for the ram 74 that corresponds to the syringe 86*a/b* that corresponds to the sensed faceplate 102*a/b*. In this regard, the power injector 40 may include a lookup table 196 (FIG. 5) in a memory unit. Such a lookup table 196 may be organized in any appropriate manner. For example, the lookup table 196 may correlate each of a plurality of syringe 86*a/b* and/or faceplate 102*a/b* types to one of a plurality of home positions. The lookup table 196 is described below with reference to FIG. 5.

The next step 130 may be for the power injector 40 to present a user of the power injector 40 with a "home" button. For example, the presented "home" button may be presented on the GUI 11, on the touch screen display 44, and/or at any other appropriate location or locations. Alternatively, the "home" button may be a dedicated button located in any appropriate location on the power injector 40. Such a dedicated button may only be active at times where it is appropriate to home the ram 74. In another alternative, the "home" button may be a "soft key" where a particular button may be designated as the "home" button at appropriate times and may be designated to perform one or more other functions at other times.

The next step 132 may be for the power injector 40 to detect the pressing of the "home" button. For example, the power injector 40 may detect when the user presses the "home" button on the GUI 11. After the pressing of the "home" button is detected, the power injector 40 may perform the step 134 of moving the ram 74 to the home position for the syringe 86*a/b* type that corresponds to the installed faceplate 102*a/b*.

After the ram 74 is moved to the home position (e.g., homed), the user may install the syringe 86*a/b* onto the faceplate 102*a/b*. The installation of the syringe 86*a/b* may include latching the syringe 86*a/b* into position by moving the appropriate handle/latch 106*a/b*. The user may then continue with a fluid injection sequence to inject Jo fluid from the syringe 86*a/b* into the patient.

Step 130 of presenting the home button and step 132 of detecting the pressing of the home button may be optional. For example, the power injector 40 may be configured to automatically perform step 134 of moving the ram 74 to the home position once the faceplate 102*a/b* has been installed (step 124), the faceplate 102*a/b* type determined (step 126), and the corresponding home position looked up (step 128). Whether, after looking up the home position (step 120), to present the home button (step 130) or to move directly to moving the ram (step 134) may be a user-selectable preference.

Figure 4:
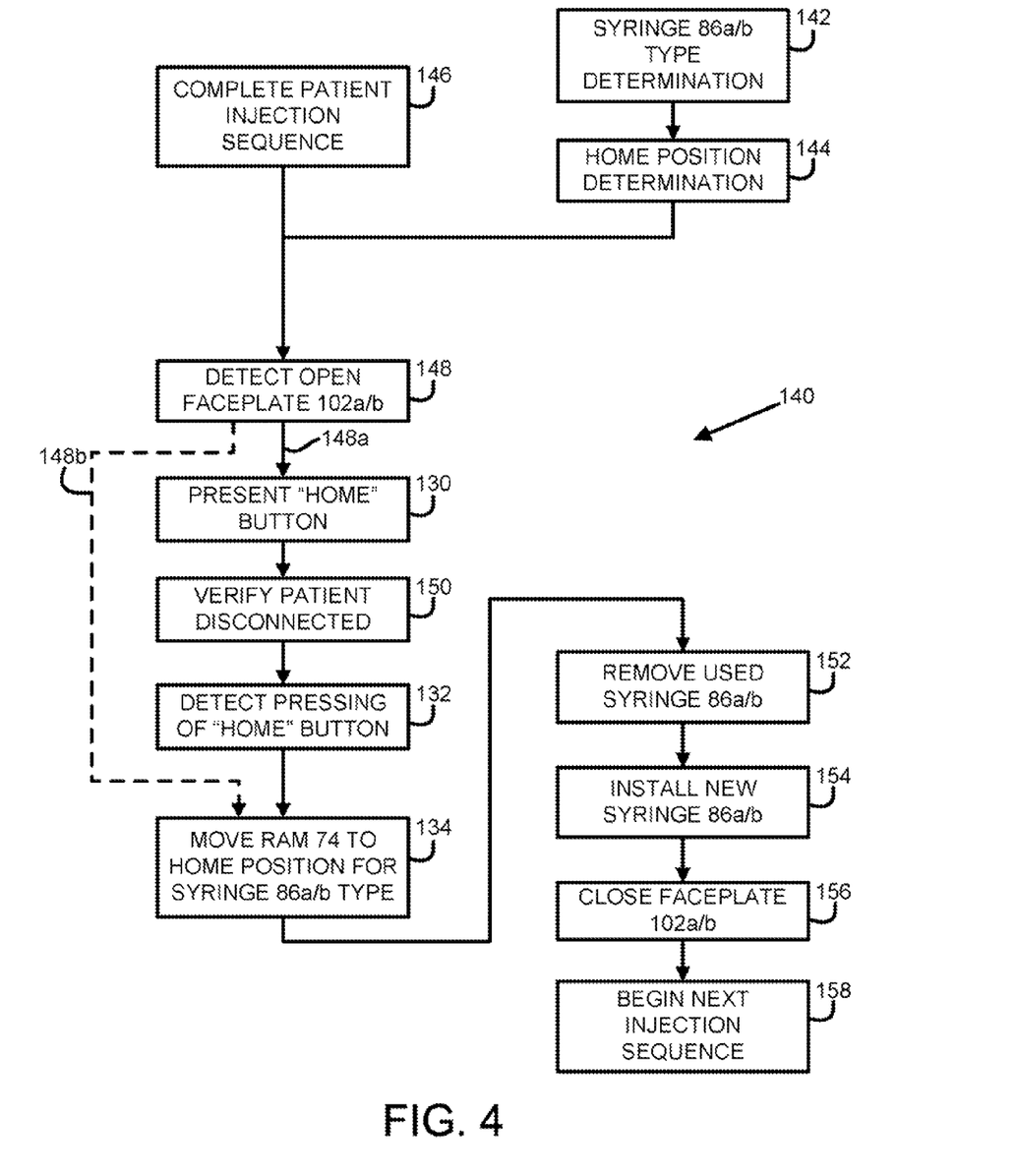
FIG. 4 is a flowchart of a method of replacing a syringe of a power injector between injection sequences.

FIG. 4 is a flowchart of a method 140 of replacing a syringe 86*a/b* of a power injector 40 between injection sequences. The individual steps of the method 140 may be performed in any appropriate order. Prior to replacing the syringe 86*a/b*, the step 142 of determining the syringe 86*a/b* type to be replaced may be performed. The syringe 86*a/b* type determination may be performed in any appropriate manner including sensing faceplate 102*a/b* type as described above with reference to step 126 of FIG. 3. For example, the method 120 of FIG. 3 may be performed prior to an initial patient injection sequence and the syringe 86*a/b* and/or faceplate 102*a/b* type may be determined during the performance of the method 120. Accordingly, the faceplate 102*a/b* and/or syringe 86*a/b* determination made during initial setup may be used in subsequent syringe 86*a/b* replacements.

In an embodiment, the syringe 86*a/b* type may be determined by input from a user. For example, where a series of patient injection sequences are to be performed using the same type of syringe 86*a/b*, the syringe 86*a/b* type inputted by the user may be used during all subsequent syringe 86*a/b* replacements.

In conjunction with the performance of step 142 of determining the syringe 86*a/b* type to be replaced, step 144 of home position determination based on the determined syringe 86 *a/b* type may also be performed. The home position determination may be performed as described above with reference to step 128 of FIG. 3.

After a patient injection sequence has been completed (step 146), the method 140 of replacing a syringe 86*a/b* may be performed. Additionally, and as noted above, syringe 86*a/b* type determination (step 142) and home position determination (step 144) may have been performed prior to the performance of the method 140 of replacing a syringe 86*a/b* of FIG. 4. Alternatively, syringe 86*a/b* type determination (step 142) and home position determination (step 144) may be performed at any appropriate time during operation of the power injector 40.

The first step 148 of the method 140 of replacing a syringe 86*a/b* may be to detect an open faceplate 102*a/b*. Opening the faceplate 102*a/b* may include manipulating (e.g., unlatching) the corresponding handle/latch 106*a/b* (described above with reference to FIG. 2B). A handle status sensor 194 (FIG. 5) of the power injector 40 may be operable to detect when the faceplate 102*a/b* is open/unlatched. For example, the handle status sensor 194 may be disposed on the power head 50 and operable to detect when the handle 106*a/b* on the faceplate 102*a/b* is in an open position. For example, the handle status sensor 194 may be disposed within the faceplate 102*a/b* and operable to send a signal or otherwise indicate to the power injector 40 that the handle 106*a/b* on the faceplate 102*a/b* is an open position. The handle status sensor 194 may also be referred to herein as a syringe latch sensor. Any other appropriate method and/or devices to determine when the handle 106*a/b* on the faceplate 102*a/b* is in an open position may be utilized by the power injector 40.

In a first embodiment of the method 140, the method 140 may proceed from step 148 along arrow 148*a*. In such an embodiment, the next step 130 may be to present a "home" button to a user of the power injector 40 as described above with reference to FIG. 3. An optional next step 150 may be to verify that the patient has been fluidly disconnected from the power injector 40. Such verification may help to ensure that no fluids are injected into or drawn from the patient during any subsequent ram 74 homing movement. Such verification may be performed by a user visually examining the patient and power injector 40. Alternate to or in addition to a user performed check, the power injector 40 may make a determination that it is no longer fluidly connected to the patient. Such a determination may be made in any appropriate manner using any appropriate sensor or sensors. The next step 132 may be for the power injector 40 to detect the pressing of the "home" button as described above with reference to FIG. 3. The "home" button may take any form such as those described above with reference to FIG. 3. After the pressing of the "home" button is detected, the power injector 40 may perform the step 134 of moving the ram 74 to the determined home position (step 144) for the determined syringe 86*a/b* type (step 142).

In an alternate embodiment (e.g., alternate to the performance of steps 130, 150 and 132 described above), the method may proceed from step 148 along arrow 148*b*. In such an alternate embodiment, the movement of the ram 74 to the home position for the determined syringe 86*a/b* type may begin upon detecting the faceplate 102*a/b* has been opened (step 148).

Whether to perform the method 140 along path 148*a* (presenting "home" button) or 148*b* (opening faceplate triggers ram 74 movement) may be based on a user-selectable preference. For example, a user of the power injector 40 may, at any appropriate time, access control software of power injector 40 and enter a preference for how the power injector 40 is to behave (follow 148*a* or 148*b*) upon detecting an open faceplate 102*a/b* (step 148).

In another embodiment, the power injector 40 may select between performing the method along arrow 148*a* and performing the method along arrow 148*b*. For example, where the power injector 40 determines that the ram 74 is within a predetermined distance from the home position, the power injector 40 may cause the ram 74 to automatically move to the home position upon detecting an open faceplate 102*a/b* (step 148). Continuing this example, where the power injector 40 determines that the ram 74 is not within the predetermined distance from the home position, the power injector 40 may perform the method 140 along arrow 148*a* and present the "home" button (step 130) to the user. Such a method may be beneficial since it may be difficult for a user to distinguish situations where the ram 74 is in the home position from situations where of the ram 74 is close to, but not in, the home position. For example, the predetermined distance may be where the plunger 90*a/b* is within about 10 ml of the home position (e.g., where the volume within the syringe 86*a/b* is within about 10 ml of the volume of the syringe 86*a/b* when the plunger 90*a/b* is in the home position).

After the ram 74 has been moved to the home position for the syringe 86*a/b* type being used, the next step 152 may be to remove the used syringe 86*a/b* from the faceplate 102*a/b*. This may be followed by the step 154 of installing a new syringe 86*a/b* and then closing (e.g., latching) the faceplate 102a/b. The next step 158 may be to begin the next injection sequence using the power injector 40 with the new syringe 86a/b.

In any of the above methods, the steps described may be performed for a single syringe in a single syringe power injector or for multiple syringes in a multiple syringe power injector. Where the methods are performed for multiple syringes in a multiple syringe power injector, any of the steps may be performed serially or in parallel where appropriate. For example, both rams 74 of the dual syringe power injector 40 of FIGS. 2A-2C may be simultaneously moved to their respective home positions upon the pressing of the "home" button. Such simultaneous movement capabilities may reduce changeover times between patients and therefore increase user and power injector efficiencies.

Figure 5:
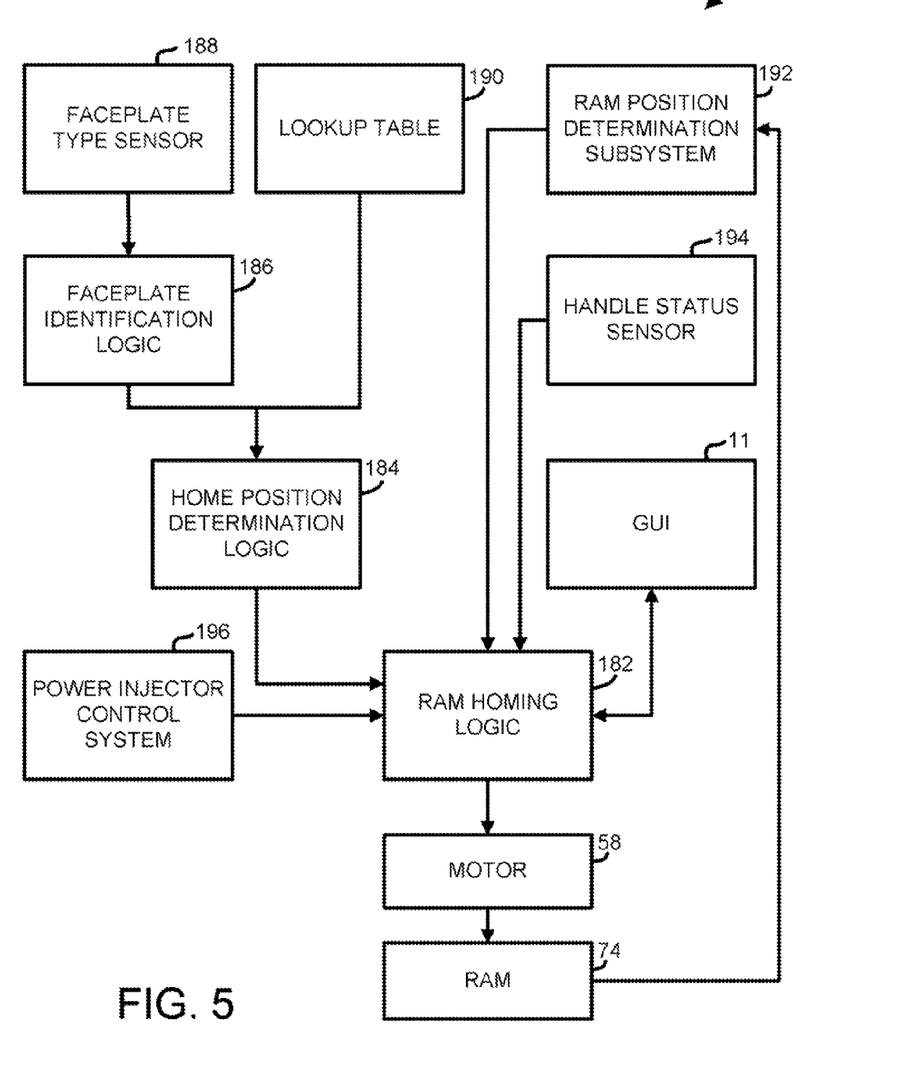
FIG. 5 is a block diagram of inputs to ram drive logic of a power injector.

FIG. 5 is a block diagram 180 of inputs to ram homing logic 182 of the power injector 40. The ram homing logic 182 may be operable to move the ram 74 (FIG. 2C) to a home position corresponding to a particular syringe 86a/b to be installed on the faceplate 102a/b. The ram homing logic 182 may be operable to move the ram 74 by driving the motor 58 (FIG. 2C).

Home position determination logic 184 may provide a target home position for use by the ram homing logic 182. The home position determination logic 184 may be operable to determine home position corresponding to the syringe 86a/b type to be connected to the faceplate 102a/b. Faceplate identification logic 186 may be operable to identifying the type of faceplate 102a/b attached to the power injector 40. The faceplate identification logic 186 may be operable to identify the type of faceplate 102a/b based on input from a faceplate type sensor 188. For example, each different type of faceplate 102a/b that may be installed onto the powerhead 50 may incorporate a unique feature that is operable to be sensed by the faceplate type sensor 188. Accordingly, a unique signal may be generated by the faceplate type sensor 188 for each unique type of faceplate 102a/b that may be installed onto the powerhead 50. The faceplate identification logic 186 may be operable to determine faceplate 102a/b type installed on the powerhead 50 based on the signal received from faceplate type sensor 188. The faceplate type sensor 188 may be of any appropriate configuration. For example, the faceplate type sensor 188 may comprise a single sensor or a group of sensors. For example, the faceplate type sensor 188 may be an optical sensor, a capacitive sensor, a sensor capable of detecting one or more magnets disposed within the faceplate 102a/b, or any other appropriate sensor or combination of sensors. The faceplate 102a/b may have specific features that enables various different types of faceplates 102a/b to be identified. For example, the faceplate 102a/b may include one or more magnets, visible features, or other features that would enable identification.

The faceplate identification logic 184 may be used to identify and distinguish between various faceplates 102a/b such that each unique faceplate 102a/b may be distinguished. Alternatively, the faceplate 102a/b identification features may be configured such that the identification feature correlates to a home position of the syringe 86a/b to be installed onto the faceplate 102a/b. In this regard and for example, where two different faceplates 102a/b are each capable of accommodating a unique syringe 86a/b type, but each of the two unique syringe 86a/b types requires the same home position, the two faceplates 102a/b may share the same faceplate 102a/b identification feature. In this regard, the power injector may not be operable to distinguish between the two types of faceplates 102a/b but it may be operable to distinguish that each of the two faceplates 102a/b requires the same home position.

Since a faceplate 102a/b may be configured to hold a particular syringe 86a/b type, identifying the faceplate 102a/b may be the functional equivalent of identifying the syringe 86a/b type that may be installed onto the faceplate. In this regard, the faceplate identification logic 184 may considered to be syringe type identification logic.

The faceplate type sensor 188 may comprise a reader that may directly read data from the faceplate 102a/b. For example, the faceplate type sensor 188 may comprise a radio frequency identification (RFID) tag reader and the faceplates 102a/b to be installed onto the powerhead 50 may include RFID tags. In this regard, the faceplate type sensor 188 may be operable to read the identity of the faceplate 102a/b. In another example, the faceplate type sensor 188 may comprise a barcode reader and the faceplate 102a/b may include a barcode.

In one embodiment, the faceplate type sensor 188 may be a sensor operable to detect magnets incorporated into the faceplates 102a/b. For example, the faceplate type sensor 188 may include sensors located in first and second positions operable to detect corresponding magnets disposed within the faceplate 102a/b. In such an example, a single magnet disposed in the first position on the faceplate 102a/b may correspond (and such corresponding may be stored in the lookup table 190 discussed below) to a first syringe 86a/b type (e.g., a syringe 86a/b that requires a home position where the ram 74 is retracted) and a single magnet disposed in the second position on the faceplate 102a/b may correspond to a second syringe 86a/b type (e.g., a syringe 86a/b that requires a home position where the ram 74 is extended). Along the same lines, two magnets, one disposed in the first position and one disposed in the second position of the faceplate 102a/b may correspond to a third syringe 86a/b type (e.g., a syringe 86a/b that requires a home position for the ram 74 between retracted and extended positions). Accordingly, using inputs from the faceplate type sensor 188 to determine whether or not magnets are disposed in the first and second positions, the faceplate identification logic 186 may be operable to distinguish between three different types of faceplates 102a/b. Additional magnet positions may be used to allow more types of faceplates 102a/b to be distinguished.

Once the faceplate identification logic 186 has identified the type of faceplate 102a/b interconnected to the powerhead 50, the identification may be forwarded to the home position determination logic 184. The home position determination logic 184 may then look up a home position in the lookup table 190 that corresponds to the identified faceplate 102a/b (and the syringe 86a/b installed thereon). The lookup table 190 may be stored in a memory unit of the power injector 40. The memory unit may be of any appropriate type, such as for example, a hard drive or a random access memory unit. The determined home position may be forwarded to the ram homing logic 182.

The power injector 40 may further include a ram position determination subsystem 192. The ram position determination subsystem 192 may include components operable to determine the position of the ram 74 relative to the powerhead 50. Such capabilities may be desirable since the position of the ram 74 at the end of an injection sequence may not be consistent from injection sequence to injection sequence and also may not be the same as the home position. It should be noted that the ram position determination subsystem 192 may also be used to monitor ram 74 position during injection sequences and other power injector 40 operations. To determine the ram 74 position, a rotary encoder may be interconnected to the drive screw 66 and the output of the rotary encoder may be directed to a processor of the power injector 40 that may be operable to determine the position of the ram 74. Other methods of ram 74 position determination may be used by the power injector 40. For example, the ram position determination subsystem 192 may use linear encoders, hall effect sensors, and/or optical sensors to determine a position of the ram 74. The ram position determination subsystem 192 may forward a current ram 74 position to the ram homing logic 182. In this regard, both the current ram 74 position and the desired home position may be inputted into the ram homing logic 182. Accordingly, the ram homing logic 182 may be operable to determine the difference between the current ram 74 position and the desired home position and the ram homing logic 182 may also be operable to determine when the current ram 74 position coincides with the desired home position.

The power injector 40 may also include the handle status sensor 194 discussed above. An output from the handle status sensor 194 may be fed into the ram homing logic 182. Accordingly, in an embodiment where it is desired for the ram 74 to be moved to the home position upon opening of the faceplate 102*a/b*, the ram homing logic 182 may be operable to cause the motor 58 to move the ram 74 to the home position (as determined by the home position determination logic 184) when the input from the handle status sensor 194 indicates that the faceplate 102*a/b* is open and that the ram 74 is not currently in the home position (determined by the ram position determination subsystem 192).

The power injector 40 may also include the GUI 11 discussed above. The GUI 11 may interact with the ram homing logic 182 as in the following example: The ram homing logic 182 may determine that the handle 106*a/b* is open (from the handle status sensor 194) and that the ram 74 is not currently in the home position (from the ram position determination subsystem 192 and the home position determination logic 184) and send a signal to the GUI 11 to present a "home" button to the user. Once the user actuates the "home" button, the GUI 11 may send an appropriate signal to the ram homing logic 182 and the ram homing logic 182 may then cause the motor 58 to move the ram 74 to the home position.

In another operational scenario, a power injector control system 196 may be operationally interconnected to the ram homing logic 182. The power injector control system 196 may be operable to send a signal to the ram homing logic 182 when an injection sequence has been completed. Upon receiving such a signal, the ram homing logic 182 may compare the ram 74 position (as determined by the ram position determination subsystem 192) to the desired home position (as determined by the home position determination logic 184) and if the two positions are within a predetermined distance from each other (e.g., 10 ml), the ram homing logic 182 may cause the motor 58 to move ram 74 to the home position (this may be done regardless of whether the faceplate 102*a/b* is open or closed).

In yet another operational scenario, the power injector control system 196 may be operable to detect the removal of the syringe 86*a/b* from the faceplate 102*a/b*. The power injector control system 196 may be operable to send a signal to the ram homing logic 182 when the syringe 86*a/b* is removed from the faceplate 102*a/b*. Upon receiving such a signal, the ram homing logic 182 may cause the motor 58 to move ram 74 to the home position.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector comprising:
   a ram;
   a syringe type identification logic;
   a memory unit, wherein said memory unit comprises a lookup table correlating each one of a plurality of syringe types to one of a plurality of home positions stored in said memory unit, wherein each one of said plurality of syringe types in said lookup table is associated with a particular one of said plurality of home positions in said lookup table, wherein said memory unit comprises a first syringe type and a corresponding first home position, wherein said memory unit comprises a second syringe type and a corresponding second home position, wherein said first and second syringe types are different, and wherein said first and second home positions are different;
   a syringe latch;
   a syringe latch sensor configured to identify when said syringe latch is in an open position, wherein a syringe may be installed on and removed from said power injector when said syringe latch is in said open position; and
   a ram homing logic in communication with said syringe latch sensor and operable to automatically drive said ram to one of said plurality of home positions corresponding to one of said plurality of syringe types: a) based upon occurrence of at least one predetermined condition, wherein said at least one predetermined condition comprises said syringe latch sensor identifying that said syringe latch has been disposed in said open position; b) said syringe latch sensor sending a communication to said ram homing logic after said syringe latch sensor identifies that said syringe latch has been disposed in said open position; and c) based upon an output of said syringe type identification logic, which identifies a syringe type of the syringe that has been installed on said power injector using said syringe latch, and which is used to retrieve a corresponding home position from said memory unit.

2. The power injector of claim 1, further comprising the syringe, wherein said at least one predetermined condition further comprises another predetermined condition that is selected from the group consisting of activation of a home button on said power injector, a completion of an injection sequence, and fluidly disconnecting a patient from said power injector.

3. The power injector of claim 1, further comprising a syringe sensor.

4. The power injector of claim 3, wherein said syringe sensor is selected from the group consisting of an optical sensor and a radio frequency identification (RFID) reader.

5. The power injector of claim 1, further comprising a ram position encoder.

6. The power injector of claim 1, wherein said syringe latch comprises a faceplate, and wherein said faceplate comprises a syringe mounting member.

7. The power injector of claim 6, wherein said faceplate is configured for said first syringe type, wherein a faceplate type of said faceplate that corresponds to said first syringe type is communicated to said power injector by said syringe type identification logic.

8. The power injector of claim 1, further comprising:
a faceplate mounting member; and
a faceplate, wherein said faceplate comprises a syringe mounting member, wherein said syringe type identification logic is operable to determine a faceplate type of said faceplate when said faceplate is interconnected to said faceplate mounting member, and wherein said syringe latch comprises said faceplate.

9. The power injector of claim 8, further comprising a faceplate sensor.

10. The power injector of claim 9, wherein said faceplate sensor is operable to sense a presence of said faceplate installed on said power injector.

11. The power injector of claim 9, wherein said faceplate sensor is operable to sense said faceplate type of said faceplate installed on said power injector.

12. The power injector of claim 9, wherein said faceplate sensor is operable to distinguish said faceplate type based on sensing at least one magnet of said faceplate.

* * * * *